United States Patent
Sakaguchi

(10) Patent No.: US 10,660,614 B2
(45) Date of Patent: May 26, 2020

(54) ULTRASONIC PROCESSING APPARATUS AND METHOD

(71) Applicant: Sony Corporation, Tokyo (JP)

(72) Inventor: Tatsumi Sakaguchi, Kanagawa (JP)

(73) Assignee: Sony Corporation, Tokyo (JP)

(*) Notice: Subject to any disclaimer, the term of this patent is extended or adjusted under 35 U.S.C. 154(b) by 947 days.

(21) Appl. No.: 14/308,882

(22) Filed: Jun. 19, 2014

(65) Prior Publication Data

US 2015/0005632 A1    Jan. 1, 2015

(30) Foreign Application Priority Data

Jun. 26, 2013    (JP) .................................. 2013-133668

(51) Int. Cl.
*A61B 8/00* (2006.01)
*A61B 8/08* (2006.01)
*G01S 7/52* (2006.01)

(52) U.S. Cl.
CPC ............ *A61B 8/485* (2013.01); *A61B 8/0858* (2013.01); *A61B 8/461* (2013.01); *A61B 8/5207* (2013.01); *G01S 7/52042* (2013.01); *G01S 7/52071* (2013.01)

(58) Field of Classification Search
CPC .. A61B 8/08; A61B 8/14; A61B 8/485; A61B 8/00; A61B 8/463; A61B 8/0858; A61B 8/469; G01S 7/52071; G01S 7/52042
See application file for complete search history.

(56) References Cited

U.S. PATENT DOCUMENTS

| 6,558,324 B1 * | 5/2003 | Von Behren ............. A61B 8/08 600/437 |
| 2011/0054314 A1 * | 3/2011 | Tanigawa ................. A61B 8/08 600/438 |

FOREIGN PATENT DOCUMENTS

| WO | WO 2005-025425 A | 3/2005 |
| WO | WO 2010-044385 A | 4/2010 |

* cited by examiner

*Primary Examiner* — Elmer M Chao
(74) *Attorney, Agent, or Firm* — Wolf, Greenfield & Sacks, P.C.

(57) ABSTRACT

An ultrasonic processing apparatus includes a viscoelastic coefficient calculation unit that calculates a viscoelastic coefficient of an object from an ultrasonic signal acquired through an oscillator of a probe; and a spatial change amount calculation unit that calculates spatial change amount of the viscoelastic coefficient calculated by the viscoelastic coefficient calculation unit and outputs the calculated spatial change amount as brightness information when displaying an image relating to the viscoelastic coefficient.

12 Claims, 7 Drawing Sheets

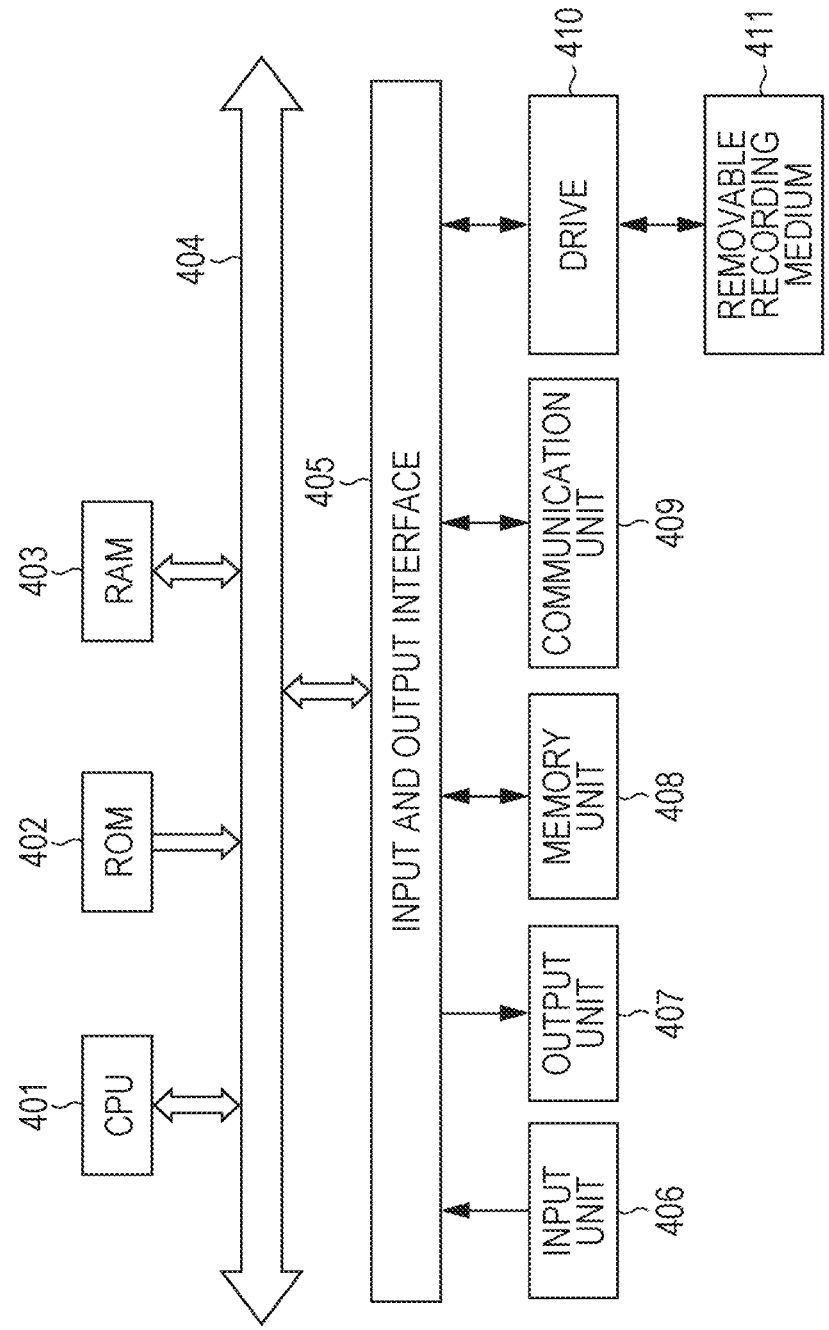

ULTRASONIC PROCESSING APPARATUS AND METHOD

CROSS REFERENCE TO RELATED APPLICATIONS

This application claims the benefit of Japanese Priority Patent Application JP 2013-133668 filed Jun. 26, 2013, the entire contents of which are incorporated herein by reference.

BACKGROUND

The present disclosure relates to an ultrasonic processing apparatus and an ultrasonic processing method, and in particular, relates to an ultrasonic processing apparatus and an ultrasonic processing method by which it is possible to more clearly depict the difference in hardness in elastography.

In the elastography that evaluates the hardness of a tissue using ultrasonic waves, information of colors (hue of a HSV color system) has been mainly used to express portions which have different hardness and distributed in the tissue.

However, there is a case where it is difficult to sufficiently detect the difference by human sight in the expression using the colors if the difference in the hardness per the portion is minor.

In order to differentially depict the portions having small differences, a system of narrowing a setting of Region of Interest (ROI) to narrow a dynamic range of a viscoelastic coefficient and subdividing gradation expression by colors is used. However, in this case, it is difficult to simultaneously express the global difference in the hardness. In addition, it is typically difficult to set the portions having the small differences as ROI and the detection time for changing the setting of ROI also increases.

Technology disclosed in International Publication No. 2010/044385 or International Publication No. 2005/025425 has been proposed. International Publication No. 2010/044385 discloses that the depiction of the portions having different hardness is clarified through appropriate setting of a threshold value by calculating a histogram of the measured elasticity.

In International Publication No. 2005/025425, technology of performing the depiction of the portions through signal processing, and superimposing the result on a display image has been proposed.

However, in the technology disclosed in International Publication No. 2010/044385, the display is optimized within the given ROI, and therefore, the view is different in global distribution of the hardness and in local distribution of the hardness. In addition, the technology disclosed in International Publication No. 2005/025425 includes a process according to various threshold values or a process based on empirical results, and therefore, there is a concern that presentation of results of a recognition process of a viscoelastic coefficient itself may mislead interpretation by a human as an inspector.

SUMMARY

As described above, it is desirable to merely present the physical amount to the extent that the inspector easily understands the physical amount in the display of the elastography (viscoelastic coefficient), and its judgment has to be dependent on the inspector. Accordingly, it is necessary to present sufficient information (group) as recognizable information for the inspector to judge the shape of the tissue.

The present disclosure can more clearly depict the difference in the hardness in the elastography.

According to an embodiment of the present disclosure, there is provided an ultrasonic processing apparatus including: a viscoelastic coefficient calculation unit that calculates a viscoelastic coefficient of an object from an ultrasonic signal acquired through an oscillator of a probe; and a spatial change amount calculation unit that calculates spatial change amount of the viscoelastic coefficient calculated by the viscoelastic coefficient calculation unit and outputs the calculated spatial change amount as brightness information when displaying an image relating to the viscoelastic coefficient.

The viscoelastic coefficient calculation unit may output the calculated viscoelastic coefficient as color information when displaying an image relating to the viscoelastic coefficient.

The spatial change amount calculation unit may calculate the spatial change amount of the viscoelastic coefficient of the object in a beam direction.

The spatial change amount calculation unit may calculate the spatial change amount of the viscoelastic coefficient of the object in an element direction.

The spatial change amount of the viscoelastic coefficient may be a differential value of the viscoelastic coefficient.

The viscoelastic coefficient may be distortion.

The viscoelastic coefficient may be an elastic modulus.

The ultrasonic processing apparatus may further include an image synthesis unit that synthesizes an image relating to the object with the brightness information which is output from the spatial change amount calculation unit and the color information which is output from the viscoelastic coefficient calculation unit.

The image relating to the object may be a brightness image acquired from the ultrasonic signal.

The image relating to the object may be an endoscopic image of the object acquired from the outside.

The viscoelastic coefficient calculation unit may output the calculated viscoelastic coefficient as depth information when displaying a stereoscopic image relating to the viscoelastic coefficient.

The ultrasonic processing apparatus may further include a display control unit that controls display of the image relating to the viscoelastic coefficient based on the brightness information output from the spatial change amount calculation unit.

According to another embodiment of the present disclosure, there is provided an ultrasonic processing method including causing an ultrasonic processing apparatus to calculate a viscoelastic coefficient of an object from an ultrasonic signal acquired through an oscillator of a probe, to calculate a spatial change amount of the calculated viscoelastic coefficient, and to output the calculated spatial change amount as brightness information when displaying an image relating to the viscoelastic coefficient.

In the embodiments of the present disclosure, the viscoelastic coefficient of the object is calculated from an ultrasonic signal acquired through the oscillator of the probe. The spatial change amount of the calculated viscoelastic coefficient is calculated and the calculated spatial change amount is output as brightness information when displaying an image relating to the viscoelastic coefficient.

According to the embodiments of the present disclosure, it is possible to display the viscoelastic coefficient as an image. In particular, it is possible to more clearly depict the difference in hardness in the elastography.

BRIEF DESCRIPTION OF THE DRAWINGS

FIG. 8 is a block diagram showing a configuration example of a computer.

DETAILED DESCRIPTION OF EMBODIMENTS

Hereinafter, embodiments of the present disclosure (which are set in the following embodiments) will be described. Description will be made in the following order.
1. First Embodiment (Ultrasonic Image Diagnosis Apparatus)
2. Second Embodiment (Computer)

First Embodiment

Configuration Example of Ultrasonic Image Diagnosis Apparatus

Figure 1:
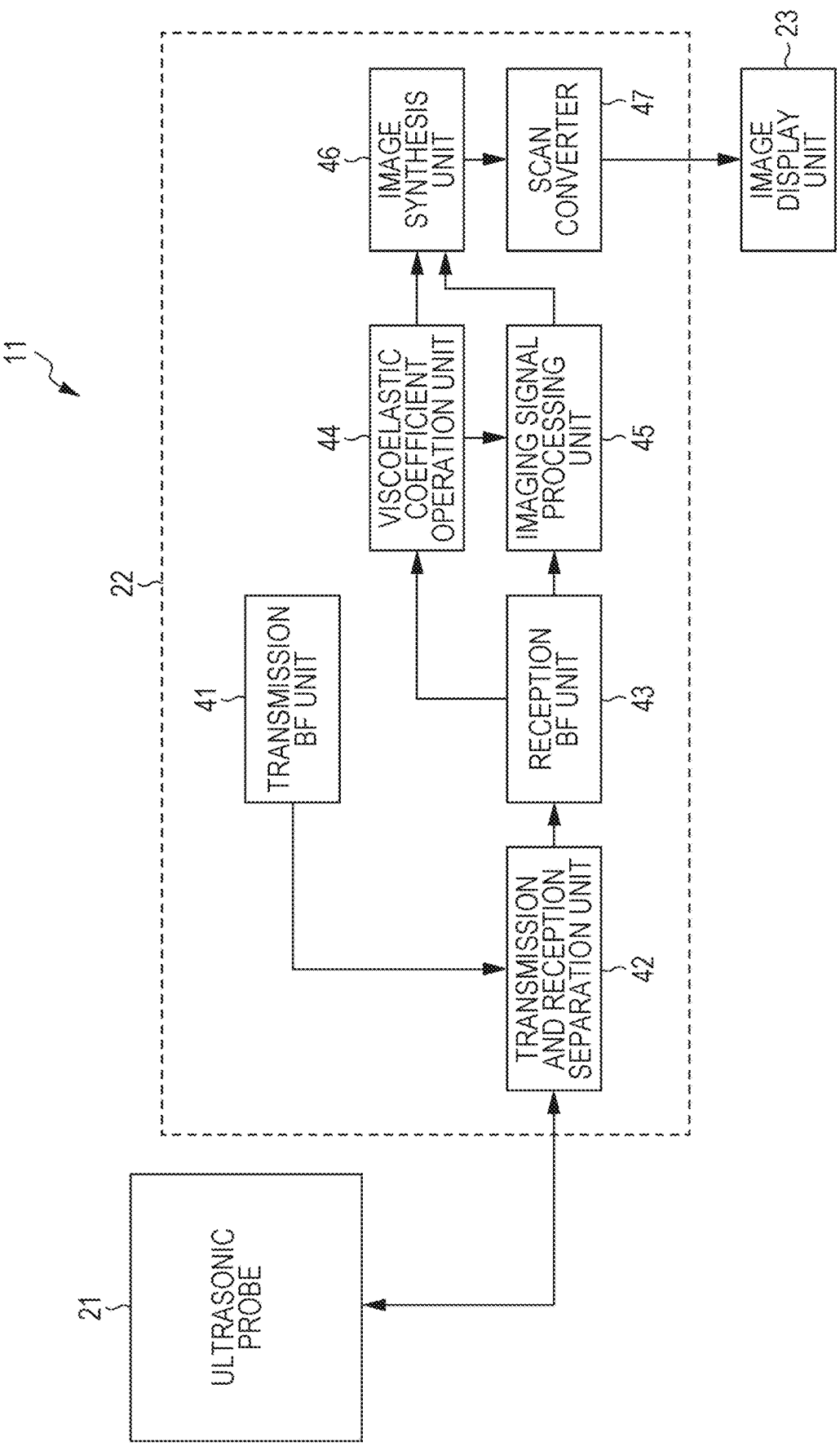
FIG. 1 is a block diagram showing a configuration example of an ultrasonic image diagnosis apparatus to which the present technology is applied.

FIG. 1 is a block diagram showing a configuration example of an ultrasonic image diagnosis apparatus as the ultrasonic processing apparatus to which the present technology is applied.

An ultrasonic image diagnosis apparatus 11 shown in FIG. 1 is an apparatus of photographing and displaying an image (that is, an ultrasonic image) inside an object (subject) using an ultrasonic wave. The ultrasonic image diagnosis apparatus 11 can be medically used in photographing an inside of a body of a patient or an unborn child, or in surgery being directly applied to an organ or a tissue, and can be industrially used in photographing a cross section of an inside of a product, for example.

In particular, the ultrasonic image diagnosis apparatus 11 photographs an ultrasonic image of an object and displays an image relating to a viscoelastic coefficient for elastography that evaluates (tests) hardness of a tissue using an ultrasonic wave. In the present specification, the viscoelastic coefficient means some coefficient that represents viscoelasticity instead of a viscoelastic modulus itself. The viscoelastic coefficient is distortion in a case of static elastography, and is an elastic module in a case of dynamic elastography, for example.

The ultrasonic image diagnosis apparatus 11 is configured to include an ultrasonic probe 21, an ultrasonic signal processing unit 22, and an image display unit 23.

The ultrasonic probe 21 is a unit of photographing an image of an object (living body; for example, the skin) while being pressed to the object. The ultrasonic probe 21 may be a 1D array or may be a 2D array.

The ultrasonic probe 21 is formed of an array oscillator in which a plurality of oscillators (transducers) are arranged, and the plurality of oscillators are arranged in a side which comes into contact with the object. The ultrasonic probe 21 sends an ultrasonic beam with respect to the object based on an ultrasonic signal from a transmission and reception separation unit 42 of an ultrasonic signal processing unit 22. In addition, the ultrasonic probe 21 receives a reflection wave (reflected and spread signal by an object) from the object and supplies the received signal to the transmission and reception separation unit 42.

The ultrasonic signal processing unit 22 is configured to include a transmission BF unit 41, a transmission and reception separation unit 42, a reception BF unit 43, a viscoelastic coefficient operation unit 44, an imaging signal processing unit 45, an image synthesis unit 46, and a scan converter 47.

The transmission BF unit 41 performs a transmission beam-forming process which is a process of generating an ultrasonic signal (waveform) and outputs the transmission beam-forming processed signal to the transmission and reception separation unit 42.

The transmission and reception separation unit 42 is a switch that can switch between transmission and reception of the ultrasonic signal. The transmission and reception separation unit 42 receives the ultrasonic signal from the transmission BF unit 41 and supplies the received ultrasonic signal to the ultrasonic probe 21. The transmission and reception separation unit 42 receives the ultrasonic signal from the ultrasonic probe 21 and supplies the received ultrasonic signal to the reception BF unit 43.

The reception BF unit 43 performs a reception beam-forming process with respect to the signal received from the transmission and reception separation unit 42. The reception beam-forming process is specifically a process of aligning phases of received waves through a process of adding each signal in which each of the received waves of the oscillators are delayed (hereinafter, appropriately referred to as a phasing addition process) based on a distance from an object point inside a measurement region to the oscillator inside the ultrasonic probe 21, and of generating a reflection wave detection signal (hereinafter, appropriately referred to as an RF signal) that shows the strength of the reflection wave from the object point inside the measurement region.

The reception BF unit 43 supplies the reception beam-forming processed RF signal (after performing phasing addition) to the viscoelastic coefficient operation unit 44 and the imaging signal processing unit 45.

The viscoelastic coefficient operation unit 44 operates a spatial differential which is a viscoelastic coefficient of (the inside of) an object including a test object and a spatial change amount thereof for elastography using the RF signal after performing the phasing addition from the reception BF unit 43. Examples of the spatial change amount include an adjacent difference or a correlation value in a vertical or horizontal direction, in addition to the spatial differential. The viscoelastic coefficient operation unit 44 outputs Hue (hue signal) that represents a viscoelastic coefficient value at a sample point on each line, Value (lightness signal) that represents a differential value of the viscoelastic coefficient, and Saturation (chroma: 1) to the image synthesis unit 46.

The imaging signal processing unit 45 performs signal processing with respect to the RF signal after performing the phasing addition from the reception BF unit 43, and converts the signal into a luminance image (B (brightness) mode image). The imaging signal processing unit 45 supplies the converted B mode image to the image synthesis unit 46.

The image synthesis unit 46 blends each value of HSV (Hue, Value (lightness or brightness), and Saturation) input from the viscoelastic coefficient operation unit 44 at a certain ratio, and further synthesizes the B mode image from the imaging signal processing unit 45 to generate an image for display. The image synthesis unit 46 color-converts the generated image for display into an RGB color system and outputs the color-converted image to the scan converter 47.

The scan converter 47 displays the image for display from the image synthesis unit 46 on an image display unit 23.

The image display unit 23 is configured to have a liquid crystal display (LCD), for example, and displays the image for display from the scan converter 47. In a case where the image display unit 23 can display a stereoscopic image, the image synthesis unit 46 may generate an image by providing the hue to each sample point as a depth value in addition to the above-described operation.

As described above, in the ultrasonic image diagnosis apparatus 11, when displaying the viscoelastic coefficient as an image (imaging the viscoelastic coefficient), Value (brightness signal) that represents the differential value of the viscoelastic coefficient is output in addition to Hue (hue signal) that represents the viscoelastic coefficient value at the sample point on each line.

Accordingly, it is possible to more clearly depict the difference in the hardness in the elastography.

Summary and Effect of the Present Technology

First, the summary and the effect of the present technology will be described with reference to FIGS. 2 and 3.

Figure 2:
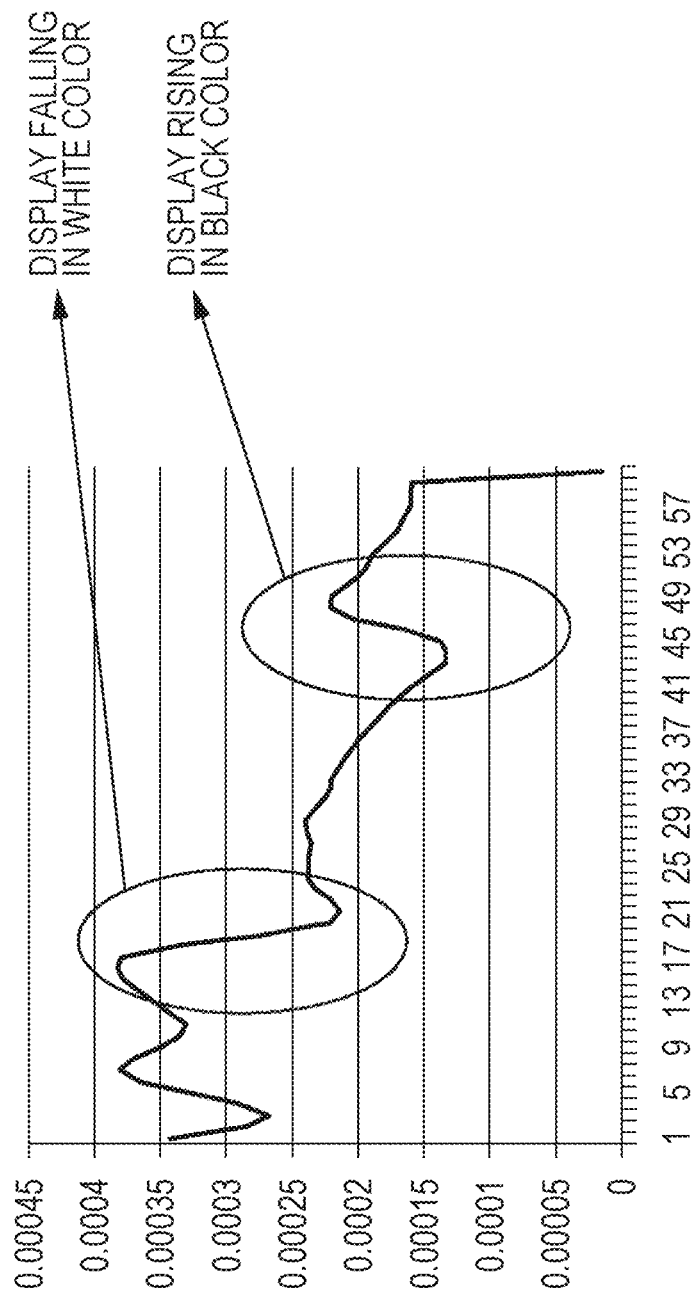
FIG. 2 is a diagram showing an example of a differential value of a viscoelastic coefficient of an object.

In FIG. 2, the vertical axis represents a differential value of a viscoelastic coefficient and the horizontal axis represents the depth of an object from the surface of the object. There are significant changes in the differential value of the viscoelastic coefficient in the vicinity of the depth 17 and the vicinity of the depth 47, and therefore, it can be seen that there are areas having different hardness from the other areas in the depth 17 or the depth 47.

Figure 3:
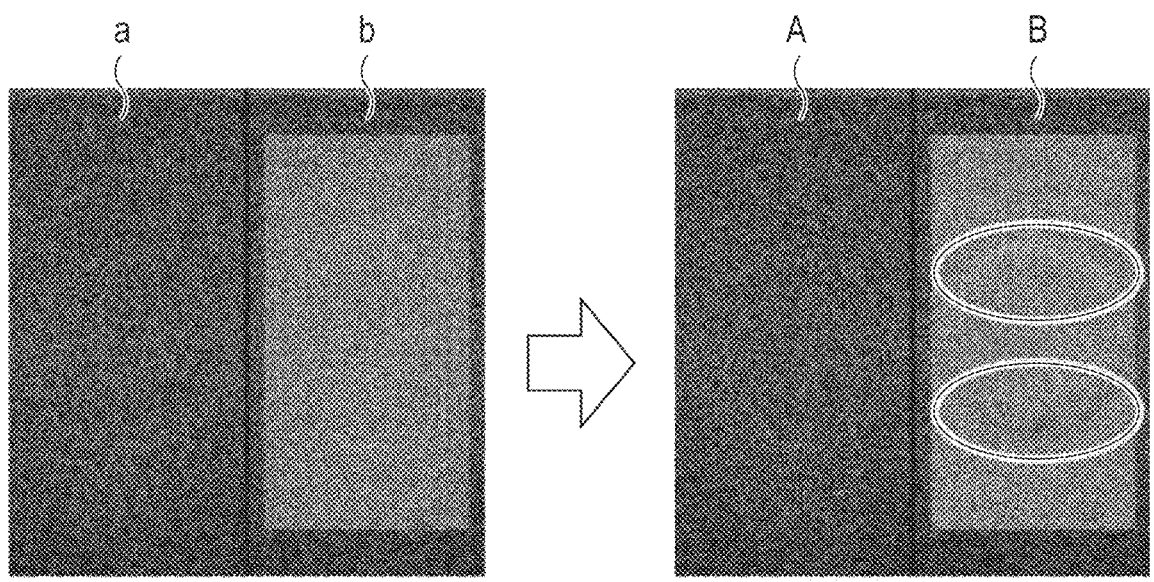
FIG. 3 is a diagram showing examples of a B mode image and a display image of a viscoelastic coefficient.

An example of FIG. 3 shows a B mode image a and a display image b of a viscoelastic coefficient according to color, and a B mode image A and a display image B according to the present technology, that is, a display image B of a viscoelastic coefficient according to the color and brightness (luminance).

The characteristic of visual perception of a human is more sensitive to the change of the luminance than the change of the color. In addition, in the characteristic of the visual perception of a human, a warm color is more sensitive to the change than a cold color in the same color.

In the case of the elastography, it is desirable to clinically find an area which is harder than its surroundings, but a cold color system is mainly assigned to a hard object, and therefore, gradation expression is weak to begin with.

In the case of the present technology, information of brightness (that is, luminance) to which the visual perception is more sensitive than the color without changing the method of mapping to Hue (color) which is already perceived as the elastography is added. Accordingly, it is possible to more clearly depict the change of the hardness.

In addition, the differential value of the viscoelastic coefficient is assigned to the brightness (luminance) instead of the viscoelastic coefficient itself. For example, as shown in FIG. 2, in the differential value of the viscoelastic coefficient, falling is displayed in white and rising is displayed in black.

Accordingly, as shown in the display image B of the viscoelastic coefficient according to the color and the brightness in FIG. 3, the vicinity of the border of the area having a different hardness becomes clear compared to the display image b of the viscoelastic coefficient according to the color, thereby supporting recognition of the shape of the area having different hardness.

Only the display image B of the viscoelastic coefficient may be displayed, but the B mode image may also be displayed on the display image B of the viscoelastic coefficient in a superimposed manner. It is possible to further clarify the vicinity of the border of the area having different hardness.

Hereinafter, specific description will be provided. The following specific description will be provided in the example of the static elastography (viscoelastic coefficient=distortion), but in the case of the dynamic elastography, it is also possible to pursue the same approach regarding the display method.

In addition, in the following, dynamic ranges of the HSV color system are described as 0 degrees (red), −120 degrees (green), and −240 degrees (blue) for Hue, 0.0 (achromatic color) and −1.0 (pure color) for Saturation, and 0.0 (minimum luminance, brightness 0, black) and −1.0 (maximum luminance, brightness 100%, white in a case of the achromatic color) for Value.

Example of Ultrasonic Signal Processing

Figure 4:
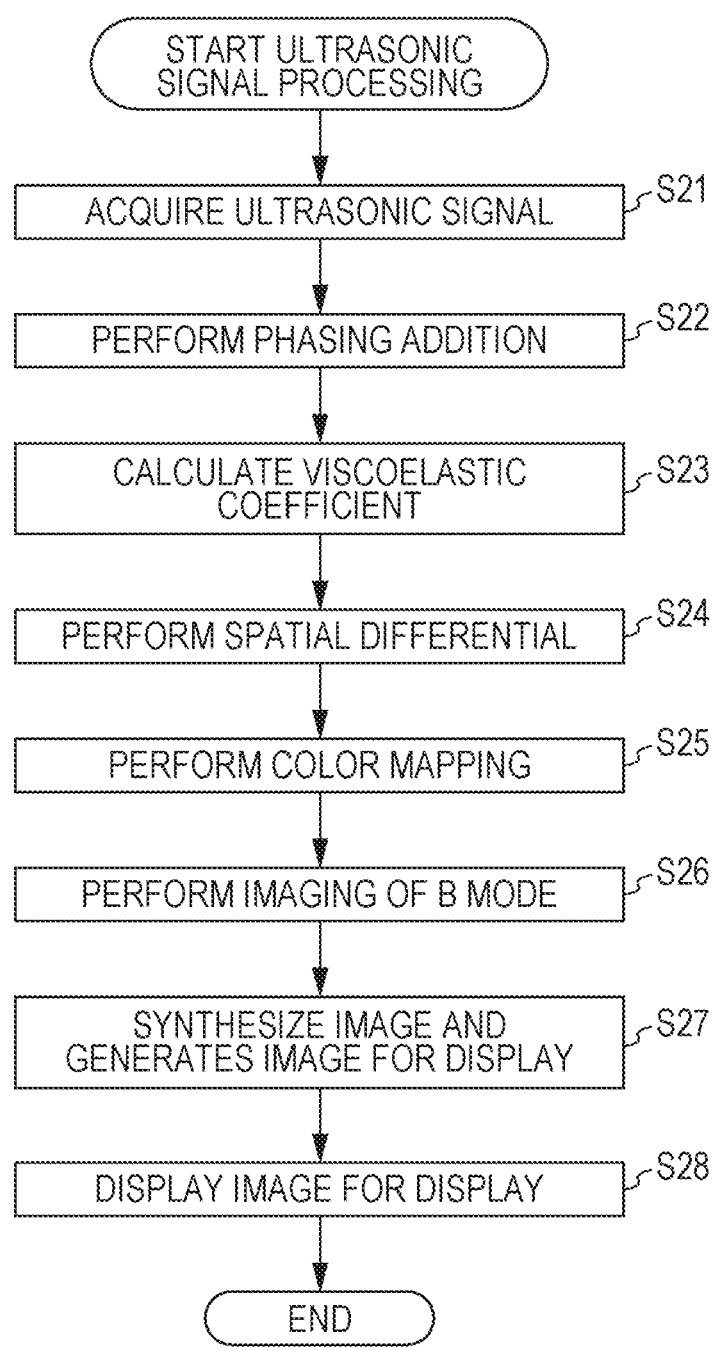
FIG. 4 is a flowchart describing an example of ultrasonic signal processing.

First, the ultrasonic signal processing for the elastography will be described with reference to the flowchart of the FIG. 4. The viscoelastic coefficient operation unit 44 when performing the ultrasonic signal processing is configured as shown in FIG. 5.

Figure 5:
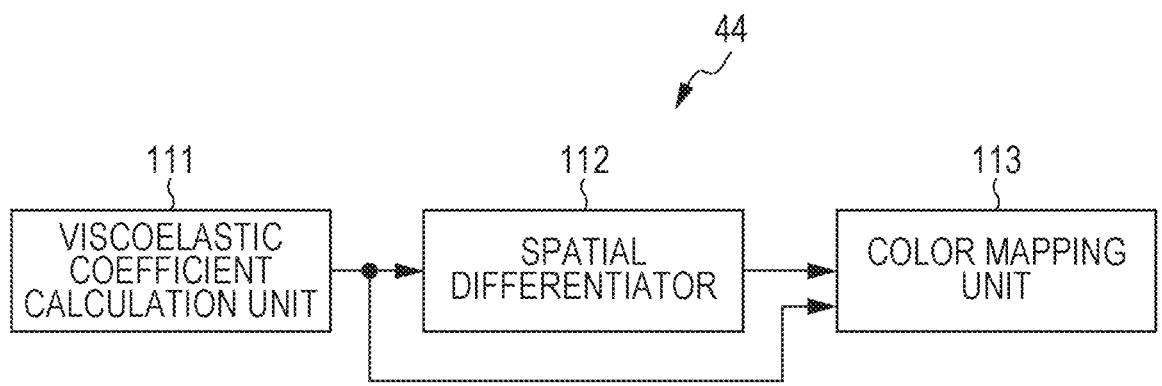
FIG. 5 is a block diagram showing a configuration example of a viscoelastic coefficient operation unit.

In the example of the FIG. 5, the viscoelastic coefficient operation unit 44 is configured so as to include a viscoelastic coefficient calculation unit 111, a spatial differential unit 112, and a color mapping unit 113.

The viscoelastic coefficient calculation unit 111 calculates the viscoelastic coefficient with respect to an input of an RF signal. The viscoelastic coefficient calculation unit 111 outputs the calculated viscoelastic coefficient to the spatial differential unit 112 and the color mapping unit 113.

The spatial differential unit 112 calculates the spatial differential with respect to the viscoelastic coefficient from the viscoelastic coefficient calculation unit 111. The spatial differential unit 112 outputs the calculated differential value to the color mapping unit 113.

The color mapping unit 113 maps the viscoelastic coefficient from the viscoelastic coefficient calculation unit 111 to Hue and maps the differential value of the viscoelastic coefficient from the spatial differential unit 112 to Value. The color mapping unit 113 outputs the mapped value of each HSV to the image synthesis unit 46. That is, the viscoelastic coefficient calculation unit 111 outputs the calculated viscoelastic coefficient to the color mapping unit 113 as color information when displaying the image relating to the viscoelastic coefficient. In addition, the spatial differential unit 112 outputs the calculated differential value to the color mapping unit 113 as brightness information when displaying the image relating to the viscoelastic coefficient.

Returning to FIG. 4, in the ultrasonic image diagnosis apparatus 11, if it is instructed to transmit the beam, the transmission BF unit 41 starts the transmission beam-forming process. In response to this, in step S21, the transmission and reception separation unit 42 acquires an ultrasonic signal.

Specifically, the transmission BF unit 41 performs the transmission beam-forming process which is a process of generating the ultrasonic signal (waveform) according to an instruction signal of a user input through an operation unit or the like (not shown) and outputs the transmission beam-forming processed signal to the transmission and reception separation unit 42. The transmission and reception separation unit 42 receives the ultrasonic signal from the transmission BF unit 41 and outputs the received ultrasonic signal to the ultrasonic probe 21.

The ultrasonic probe 21 sends an ultrasonic beam with respect to the object based on the ultrasonic signal from a transmission and reception separation unit 42. In addition, the ultrasonic probe 21 receives a reflection wave (reflected and spread signal by an object) from the object and supplies the received signal to the transmission and reception separation unit 42. The transmission and reception separation unit 42 acquires the ultrasonic signal from the ultrasonic probe 21 and supplies the acquired ultrasonic signal to the reception BF unit 43.

In step S22, the reception BF unit 43 performs the phasing addition of the ultrasonic signal from the transmission and reception separation unit 42. That is, the reception BF unit 43 performs the reception beam-forming process with respect to the ultrasonic signal from the transmission and reception separation unit 42 and supplies the reception beam-forming processed RF signal (after performing the phasing addition) to the viscoelastic coefficient operation unit 44 and the imaging signal processing unit 45.

In step S23, the viscoelastic coefficient calculation unit 111 of the viscoelastic coefficient operation unit 44 calculates the viscoelastic coefficient from the RF signal after performing the phasing addition from the reception BF unit 43. Methods of appropriately calculating the viscoelastic coefficient vary, and are omitted herein. The viscoelastic coefficient obtained herein is represented by Formula (1).

$$\varepsilon(t,e) \quad (1)$$

Here, t represents the time (and at the same time, the distance in a depth direction) and e represents the position in an array direction.

The viscoelastic coefficient calculation unit 111 outputs the calculated viscoelastic coefficient to the spatial differential unit 112 and the color mapping unit 113.

In step S24, the spatial differential unit 112 performs the spatial differential. That is, the spatial differential unit 112 calculates the spatial differential with respect to the viscoelastic coefficient from the viscoelastic coefficient calculation unit 111.

To be more specific, there are two cases which are a first method of calculating only the spatial differential in a depth direction (that is, beam direction) and a second method of calculating the spatial differential in an element direction in addition to the spatial differential in the depth direction. The spatial differential in the depth direction is represented by Formula (2) and the spatial differential of the case of adding the spatial differential in the element direction to the spatial differential in the depth direction is represented by Formula (3).

$$\frac{\partial \varepsilon}{\partial t} \quad (2)$$

$$k\frac{\partial \varepsilon}{\partial t} + (1-k)\frac{\partial \varepsilon}{\partial e} \quad (3)$$

Here, k represents a blending ratio in the depth direction and the element direction.

In addition, Formula (2) can be obtained by the following Formulas (4) and (5) as a discrete value.

$$\frac{\partial \varepsilon}{\partial t} = \varepsilon(t-1, e) - \varepsilon(t, e) \quad (4)$$

$$\frac{\partial \varepsilon}{\partial e} = \varepsilon(t, e+1) - \varepsilon(t, e) \quad (5)$$

Figure 6:
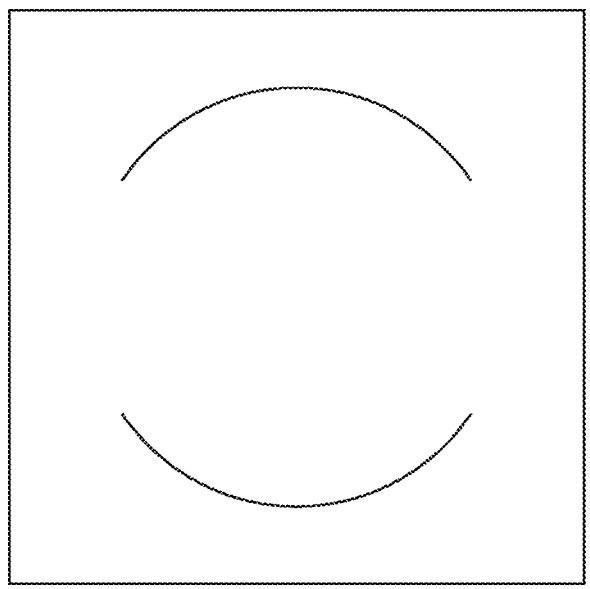
FIG. 6 is a diagram showing an example of expression according to a spatial differential in a depth direction.
Figure 7:
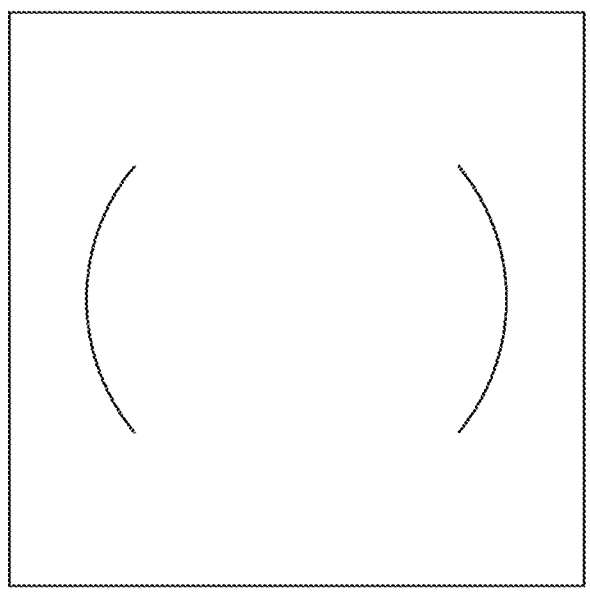
FIG. 7 is a diagram of showing an example of expression according to a spatial differential in an element direction.

With such a configuration, in the case of the first method, it is possible to express the difference in the hardness in a vertical direction as shown in FIG. 6, and specifically, the upper side is expressed to be brighter and the lower side is expressed to be darker among the borders of the object which is harder than the surroundings. In addition, in the case of the second method, it is possible to express the difference in the hardness in a horizontal direction as shown in FIG. 7 in addition to the case of the first method, and specifically, the right side is expressed to be brighter and the left side is expressed to be darker among the borders of the object which is harder than the surroundings. The configuration may be provided in reverse, but a hard substance tends to be recognized to be protruded to the front in the above-described configuration.

The spatial differential may be obtained through a third method of calculating only the spatial differential in the element direction. The border in the element direction is not detected by the B mode image, and therefore, it is possible to improve the degree of recognition of the hard substance in the element direction.

In addition, the viscoelastic coefficient ε and the spatial differential value ε' are described beforehand. The spatial differential unit 112 outputs the calculated differential value ε' to the color mapping unit 113.

Returning to FIG. 5, the color mapping unit 113 performs color mapping in step S25. That is, the color mapping unit 113 maps the viscoelastic coefficient from the viscoelastic coefficient calculation unit 111 to Hue and maps the differential value of the viscoelastic coefficient from the spatial differential unit 112 to Value. At this time, Saturation is typically set to 1.

The Hue value is mapped as shown in the following Formula (6).

$$d\varepsilon = \varepsilon_{center} - \varepsilon \quad (6)$$

$$\text{Hue}_\varepsilon = \begin{cases} d\varepsilon/N_{hard} & (d\varepsilon \geq 0) \\ d\varepsilon/N_{soft} & (d\varepsilon < 0) \end{cases}$$

Here, $\varepsilon_{center}$ is a reference value of normalization. $\varepsilon_{center}$ may be an average value of ε within a frame and may be a numerical value which is empirically obtained. $N_{hard}$ and $N_{soft}$ are respectively normalized numbers in a side harder than and a side softer than that of the reference value. $N_{hard}$ and $N_{soft}$ may be set to be adaptively controlled according to the average value and may be set as a fixed value. In addition, $N_{hard}$ and $N_{soft}$ may be the same as each other. The result of the normalization according to $\varepsilon_{center}$ and N is set to be within ranges of 0 to 120 (center) and 0 to 240.

Meanwhile, the Value is similarly mapped as shown in the following Formula (7).

$$\text{Value}_\varepsilon = \varepsilon'/N_{diff} + 0.5 \quad (7)$$

Here, $N_{diff}$ is set such that $\text{Value}_\varepsilon$ is within a range of 0.0 to 1.0.

The color mapping unit 113 outputs the mapped values of each HSV to the image synthesis unit 46.

In step S26, the imaging signal processing unit 45 performs B mode imaging. That is, the imaging signal processing unit 45 performs signal processing such as detection or filtering with respect to the RF signal after performing the phasing addition from the reception BF unit 43, and converts the signal into a luminance image (B (brightness) mode image).

Then, the imaging signal processing unit 45 maps Brightness to $Value_B$ as shown in the following Formula (8).

$$Value_B = Brightness \quad (8)$$

However, Brightness is already set to be normalized in a range of 0.0 to 1.0. In the imaging signal processing unit 45, Hue and Saturation are not output.

The imaging signal processing unit 45 outputs the mapped $Value_B$ to the image synthesis unit 46.

In step S27, the image synthesis unit 46 synthesizes HSV from the color mapping unit 113 and $Value_B$ from the imaging signal processing unit 45 as shown in the following Formula (9) to generate an image for display. The viscoelastic coefficient is not limited to being calculated by every point observed by setting of ROI (Region of Interest: attention region) or the like. For this reason, the synthesis result changes depending on the presence and absence of the output of the viscoelastic coefficient operation unit 44.

$$Hue = \begin{cases} Hue_\varepsilon & \text{if } Hue_\varepsilon \text{ exist} \\ 120 & \text{if } Hue_\varepsilon \text{ not exist} \end{cases} \quad (9)$$

$$Saturation = \begin{cases} Saturation_\varepsilon & \text{if } Saturation_\varepsilon \text{ exist} \\ 0.0 & \text{if } Saturation_\varepsilon \text{ not exist} \end{cases}$$

$$Value =$$
$$\begin{cases} m((Value_B - 0.5)Gain_B + Center_B) + (1-m)Value_\varepsilon & \text{if } Value_\varepsilon \text{ exist} \\ Value_B & \text{if } Value_\varepsilon \text{ not exist} \end{cases}$$

However, m is a coefficient that indicates what degree of the strength of the B mode is to be reflected to the entire Value. m=0.0 indicates that the luminance is determined only by ε' without superimposing the B mode image onto the result of the elastography. m=1.0 indicates that the luminance is determined only by the B mode and is not dependent on ε'.

In addition, in the equation of $(Value_B - 0.5)Gain_B + Center_B$, if Value is set as the value of the B mode as it is during the expression of the elastography, a case where a color is not almost smeared in an area having low luminance on the B mode is prevented, and therefore, a median value is raised to a high value with respect to a pixel having the result of the elastography.

The image synthesis unit 46 converts the values of Hue, Saturation, and Value which are obtained as described above to RGB values and outputs the converted RGB values to the scan converter 47 as the image for display.

In step S28, the scan converter 47 displays the image for display (RGB value) from the image synthesis unit 46 on the image display unit 23 configured to have an LCD or the like.

As described above, the characteristic of the visual perception of a human is more sensitive to the change of the luminance than the change of the color. In addition, in the characteristic of the visual perception of a human, the warm color is more sensitive to the change than the cold color in the same color.

In the present technology, the information of the brightness (that is, luminance) to which the visual perception is more sensitive than the color without changing the method of mapping to Hue (color) which is already perceived as the elastography is added. Accordingly, it is possible to more clearly depict the difference in the hardness.

In addition, the differential value of the viscoelastic coefficient is assigned to the brightness (luminance) instead of the viscoelastic coefficient itself. Therefore, the vicinity of the border of the area having a different hardness becomes clear, thereby supporting the recognition of the shape of the area having a different hardness. It is possible to exactly recognize the change of the hardness in the vicinity of the border as well due to the characteristic of the perception which is sensitive to the change of the luminance. For this reason, it is possible to increase information such as the moisture level of a lesion, the information being factors in a decision compared to ordinary elastography (only with Hue).

Furthermore, the display according to the present technology induces a pseudo stereoscopic appearance even in a case of displaying on an ordinary display (monitor). That is, the display provides an effect that the hard area looks further protruded to the front than the surroundings.

The display method according to the present technology can produce an emphasis effect of the stereoscopic appearance even when presenting the result of the elastography with respect to the display capable of performing stereoscopic display. It is possible to perform expression equivalent to a rendering to which a pseudo lighting model is defined by further superimposing the differential value on the luminance compared to a case of performing stereoscopic expression by assigning the viscoelastic coefficient value itself to the depth. Through the expression, it is possible to perceive the difference in the viscoelastic coefficient of the tissue as a geometric concave and convex shape, and therefore, it is possible to further increase the capability of presenting the information to the inspector.

According to the present technology as described above, it is possible to more clearly depict the difference in the hardness in the elastography. Accordingly, it is possible to improve inspection accuracy, for example, to prevent missing any lesion.

In the above description, the example of the HSV color system has been described. The present technology can be applied to, for example, a YUV color system or color space as long as the color system or color space uses the color or the luminance.

In addition, similarly, it is also possible to express an object not only by assigning the viscoelastic coefficient to the color and further assigning the spatial differential to the brightness when displaying a screen of the viscoelastic coefficient, but also by, for example, assigning the spatial differential to the brightness even during the stereoscopic expression by using the viscoelastic coefficient as the depth information of a stereoscopic video and by combining with a 3D display control apparatus or the like as described above.

Furthermore, the example of the display by synthesizing the B mode image with the viscoelastic coefficient value, the differential value of the viscoelastic coefficient, and HSV to which 1 is assigned has been described in the above-described description, but the display may also be performed without synthesizing the B mode image. In addition, the image to be synthesized is not limited to the B mode image, and any image may be synthesized. Specifically, it is possible to synthesize a CT image of an object, an MRI image of an object, an endoscopic image of an object (a video image or a still image photographed using an endoscope) or the like as an image relating to the object, with the viscoelastic coefficient value, the differential value of the viscoelastic coefficient, and HSV to which 1 is assigned.

The present technology can be used as any medical application or non-medical application. In addition, the present technology can be used in various situations of photographing a cross section of an object such as not only a human, but also an animal or a plant, and an artifact, using an ultrasonic wave.

The above-described series of processes can also be executed using hardware, and can also be executed using software. In the case of executing the series of processes using the software, a program which is configured to have the software is installed in a computer. Here, the computer includes a dedicated computer in which the program is incorporated into the hardware, a general purpose personal computer capable of executing various functions by installing various programs, or the like.

Second Embodiment

Configuration Example of Computer

FIG. 8 is a block diagram showing a configuration example of hardware of a computer that can execute the above-described series of processes using the program.

In the computer, a Central Processing Unit (CPU) 401, a ROM (Read Only Memory) 402, and a RAM (Random Access Memory) 403 are mutually connected through a bus 404.

The bus 404 is further connected to an input and output interface 405. The input and output interface 405 is connected to an input unit 406, an output unit 407, a memory unit 408, a communication unit 409, and a drive 410.

The input unit 406 is formed of a keyboard, a mouse, a microphone, or the like. The output unit 407 is formed of a display, a speaker, or the like. The memory unit 408 is formed of a hard disk or a nonvolatile memory. The communication unit 409 is formed of a network interface or the like. The drive 410 drives a removable recording medium 411 such as a magnetic disk, an optical disc, a magneto-optical disk, a semiconductor memory, or the like.

In the computer having the above-described configuration, the above-described series of the processes are performed by the CPU 401 through execution performed by loading the program stored in the memory unit 408 into the RAM 403 through the input and output interface 405 and the bus 404, for example.

It is possible to supply the program which is executed by the computer (CPU 401) by recording the program in the removable recording medium 411 as a package media, for example. In addition, it is possible to supply the program through a wired or wireless transmission medium such as a local area network, the Internet, and a digital broadcast.

In the computer, it is possible to install the program in the memory unit 408 through the input and output interface 405 by mounting the removable recording medium 411 in the drive 410. In addition, it is possible to install the program in the memory unit 408 by the program being received using the communication unit 409 through the wired or wireless transmission medium. In addition, it is possible to install the program in advance in the ROM 402 or the memory unit 408.

The program which is executed by the computer may be a program in which processing is performed in time series along the order described in the present specification, and may be a program in which processing is performed in parallel or at a necessary timing such as when being called.

In addition, in the present specification, the term of a system refers to an overall apparatus configured to have a plurality of apparatuses, blocks, and units.

The embodiments in the present disclosure are not limited to the above-described embodiments and various modifications can be made within the scope not departing from the gist of the present disclosure.

The preferred embodiments of the present disclosure have been described in detail with reference to the accompanying drawings, but the present disclosure is not limited to the embodiments. It is obvious that various modification examples or revised examples can be conceived by those having ordinary knowledge in the technical field to which the present disclosure belongs, within the category of technical ideas which is described in the claims, and it is naturally understood that the modification examples or the revised examples also belong to the technical scope of the present disclosure.

The present disclosure can have the following configuration.

(1) An ultrasonic processing apparatus including:

a viscoelastic coefficient calculation unit that calculates a viscoelastic coefficient of an object from an ultrasonic signal acquired through an oscillator of a probe; and a spatial change amount calculation unit that calculates spatial change amount of the viscoelastic coefficient calculated by the viscoelastic coefficient calculation unit and outputs the calculated spatial change amount as brightness information when displaying an image relating to the viscoelastic coefficient.

(2) The ultrasonic processing apparatus according to the above (1), in which the viscoelastic coefficient calculation unit outputs the calculated viscoelastic coefficient as color information when displaying an image relating to the viscoelastic coefficient.

(3) The ultrasonic processing apparatus according to the above (1) or (2), in which the spatial change amount calculation unit calculates the spatial change amount of the viscoelastic coefficient of the object in a beam direction.

(4) The ultrasonic processing apparatus according to any one of the above (1) to (3), in which the spatial change amount calculation unit calculates the spatial change amount of the viscoelastic coefficient of the object in an element direction.

(5) The ultrasonic processing apparatus according to any one of the above (1) to (4), in which the spatial change amount of the viscoelastic coefficient is a differential value of the viscoelastic coefficient.

(6) The ultrasonic processing apparatus according to any one of the above (1) to (5), in which the viscoelastic coefficient is distortion.

(7) The ultrasonic processing apparatus according to any one of the above (1) to (5), in which the viscoelastic coefficient is an elastic modulus.

(8) The ultrasonic processing apparatus according to any one of the above (1) to (7), further including:

an image synthesis unit that synthesizes an image relating to the object with the brightness information which is output from the spatial change amount calculation unit and the color information which is output from the viscoelastic coefficient calculation unit.

(9) The ultrasonic processing apparatus according to the above (8), in which the image relating to the object is a brightness image acquired from the ultrasonic signal.

(10) The ultrasonic processing apparatus according to the above (8), in which the image relating to the object is an endoscopic image of the object acquired from the outside.

(11) The ultrasonic processing apparatus according to the above (1), in which the viscoelastic coefficient calculation unit outputs the calculated viscoelastic coefficient as depth information when displaying a stereoscopic image relating to the viscoelastic coefficient.

(12) The ultrasonic processing apparatus according to any one of the above (1) to (11), further including:

a display control unit that controls display of the image relating to the viscoelastic coefficient based on the brightness information output from the spatial change amount calculation unit.

(13) An ultrasonic processing method, in which an ultrasonic processing apparatus calculates a viscoelastic coefficient of an object from an ultrasonic signal acquired through an oscillator of a probe, calculates a spatial change amount of the calculated viscoelastic coefficient, and outputs the calculated spatial change amount as brightness information when displaying an image relating to the viscoelastic coefficient.

It should be understood by those skilled in the art that various modifications, combinations, sub-combinations and alterations may occur depending on design requirements and other factors insofar as they are within the scope of the appended claims or the equivalents thereof.

What is claimed is:

1. An ultrasonic processing apparatus comprising:
    circuitry configured to:
        receive an RF signal based on an ultrasonic wave reflected from an object;
        calculate viscoelastic coefficient values of the object at different sample points in a measurement region based on the received RF signal;
        calculate spatial differential values of the viscoelastic coefficient values at the different sample points in the measurement region;
        perform color mapping of the viscoelastic coefficient values to hue values and color mapping of the spatial differential values of the viscoelastic coefficient values to brightness values; and
        generate an output image signal to display an image of the object based on the color mapped hue values and the color mapped brightness values.

2. The ultrasonic processing apparatus according to claim 1,
    wherein the circuitry is configured to calculate the spatial differential values of the viscoelastic coefficient values in a beam direction.

3. The ultrasonic processing apparatus according to claim 1,
    wherein the circuitry is configured to calculate the spatial differential values of the viscoelastic coefficient values in an element direction.

4. The ultrasonic processing apparatus according to claim 1,
    wherein the viscoelastic coefficient values include distortion.

5. The ultrasonic processing apparatus according to claim 1,
    wherein the viscoelastic coefficient values include an elastic modulus.

6. The ultrasonic processing apparatus according to claim 1,
    wherein the image is a brightness image acquired from the ultrasonic wave.

7. The ultrasonic processing apparatus according to claim 1,
    wherein the image of the object is acquired from the outside.

8. The ultrasonic processing apparatus according to claim 1,
    wherein the circuitry is configured to output the viscoelastic coefficient values as depth information when displaying a stereoscopic image relating to the viscoelastic coefficient values.

9. The ultrasonic processing apparatus according to claim 1, wherein the circuitry is configured to obtain a saturation information and to output the image further based on the saturation information.

10. The ultrasonic processing apparatus according to claim 1, wherein
    the circuitry is configured to increase the brightness of a region with high spatial differential values of the viscoelastic coefficient values in the image.

11. The ultrasonic processing apparatus according to claim 1, wherein
    the circuitry is configured to decrease the brightness of a region with low spatial differential values of the viscoelastic coefficient values in the image.

12. The ultrasonic processing apparatus according to claim 1, wherein a first region with high spatial differential values of the viscoelastic coefficient values is displayed in the image with higher brightness and a second region with low spatial differential values of the viscoelastic coefficient values is displayed in the image with lower brightness.

* * * * *